United States Patent
Kondou et al.

(10) Patent No.: US 6,445,452 B1
(45) Date of Patent: Sep. 3, 2002

(54) DEVICE FOR CHECKING SHEET PACKAGING

(75) Inventors: Kiyoyuki Kondou, Tokyo; Minoru Ito, Kanagawa, both of (JP)

(73) Assignee: Yuki Engineering System Co., Ltd., Hachioji (JP)

( * ) Notice: Subject to any disclaimer, the term of this patent is extended or adjusted under 35 U.S.C. 154(b) by 0 days.

(21) Appl. No.: 09/446,010

(22) PCT Filed: Jun. 17, 1998

(86) PCT No.: PCT/JP98/02678

§ 371 (c)(1),
(2), (4) Date: Dec. 16, 1998

(87) PCT Pub. No.: WO98/58241

PCT Pub. Date: Dec. 23, 1998

(30) Foreign Application Priority Data

Jun. 17, 1997 (JP) ............................................. 9-159532
Nov. 7, 1997 (JP) ............................................. 9-305168

(51) Int. Cl.[7] .............................................. G01N 21/88
(52) U.S. Cl. ................. 356/430; 356/237.1; 356/239.1
(58) Field of Search ........................... 356/237.1, 237.2, 356/237.3, 237.4, 237.5, 239.1, 239.3, 239.4, 239.5, 239.6, 239.7, 239.8, 429, 430, 431

(56) References Cited

U.S. PATENT DOCUMENTS

| | | | |
|---|---|---|---|
| 4,549,206 A | * 10/1985 | Suzuki et al. | 348/126 |
| 5,021,645 A | 6/1991 | Satula et al. | 250/223 R |
| 5,268,735 A | * 12/1993 | Hayashi | 356/239.1 |

FOREIGN PATENT DOCUMENTS

| | | |
|---|---|---|
| GB | 2 095 828 | 10/1982 |
| GB | 2 261 505 A | 5/1993 |
| JP | 54-143193 | 11/1979 |
| JP | 63-18568 | 5/1988 |
| JP | 5-87546 | 4/1993 |
| JP | 5-149883 | 6/1993 |
| JP | 7-209196 | 8/1995 |
| JP | 7-311160 | 11/1995 |
| JP | 8-21805 | 1/1996 |
| JP | 8-334469 | 12/1996 |

* cited by examiner

Primary Examiner—Richard A. Rosenberger
(74) Attorney, Agent, or Firm—Armstrong, Westerman & Hattori, LLP

(57) ABSTRACT

A device for checking sheet packaging, whereby all the defects of packaged articles or sheets are easily and highly accurately detected based on the density or color distribution of reflection and transmission images. Defects such as deformation, discoloration, foreign matters and contamination of an article (16) packaged with a sheet and the sheet are detected by forming a density distribution code image or color code distribution image or by executing inter-image calculation based on a reflection image, a transmission image, or density or color images thereof. The upper and lower light sources are simultaneously turned on to separately form a reflection image and a transmission image from the input image in order to enhance the checking efficiency. Furthermore, a reflector (17) is disposed under a packaging sheet to enhance image contrast and to improve checking efficiency and stability. Optimum conditions for the kind and position of the reflector are clarified.

23 Claims, 15 Drawing Sheets

|  | J2 | J1 | G1 | G2 | T | H1 | H2 | F | P | F | F | H2 | H1 | I | N | S |
|---|---|---|---|---|---|---|---|---|---|---|---|---|---|---|---|---|
| 2-BIT CODING | 01 | 01 | 10 | 00 | 10 | 10 | 00 | 11 | 01 | 11 | 11 | 00 | 10 | 0'1 | 0'1 | 01 |
| NEIGHBORING CODING | 10 | 11 | 10 | 10 | / | 01 | 01 | 01 | / | 01 | 01 | 01 | 01 | 01 | 01 | / |
| 4-BIT CODING | 0110 | 0111 | 1010 | 0010 | / | 1001 | 0'001 | 1101 | / | 1101 | 1101 | 0'001 | 1001 | 0'101 | 0'101 | / |

FIG. 11

| REFLECTED RAY | TRANSMITTED RAY | F | J1 | J2 | G1 | G2 | H1 | H2 | I | N |
|---|---|---|---|---|---|---|---|---|---|---|
| SMALL | LARGE | ○ | ○ | ○ | × | ○ | ○ | ○ | × | × |
| | | ○ | △ | △ | × | ○ | △ | ○ | △ | △ |
| MEDIUM | MEDIUM | ○ | × | × | × | ○ | × | ○ | △ | △ |
| | | ○ | × | × | × | ○ | △ | ○ | △ | △ |
| LARGE | SMALL | ○ | × | × | × | ○ | ○ | ○ | ○ | ○ |

| | | J2 | J1 | G1 | G2 | T | H1 | H2 | F | P | F | F | H2 | H1 | I | N | S |
|---|---|---|---|---|---|---|---|---|---|---|---|---|---|---|---|---|---|
| COLOR CODE | REFLECTED RAY IMAGE | 100 | 100 | 111 | 000 | 001 | 111 | 000 | 111 | 100 | 111 | 111 | 000 | 111 | 000 | 100 | 100 |
| | TRANSMITTED RAY IMAGE | 100 | 100 | 000 | 000 | 000 | 000 | 000 | 100 | 100 | 100 | 100 | 000 | 000 | 000 | 100 | 100 |
| | COMBINATION (OCTAL) | 44 | 44 | 70 | 00 | 10 | 70 | 00 | 74 | 44 | 70 | 70 | 00 | 70 | 00 | 44 | 44 |

F I G. 14
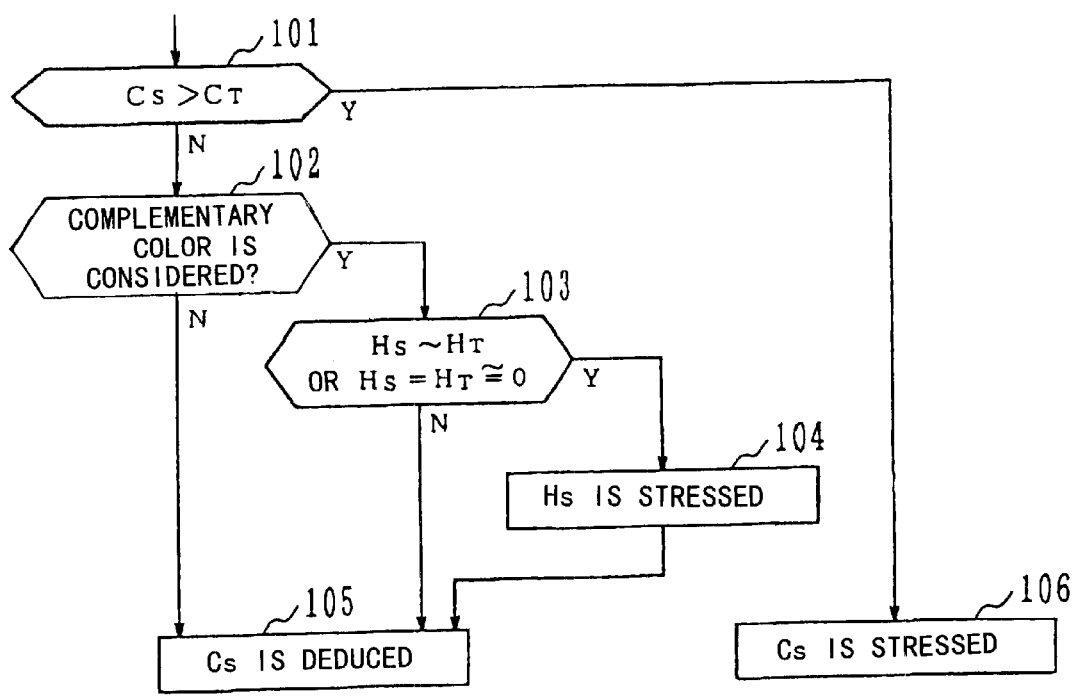

F I G. 15
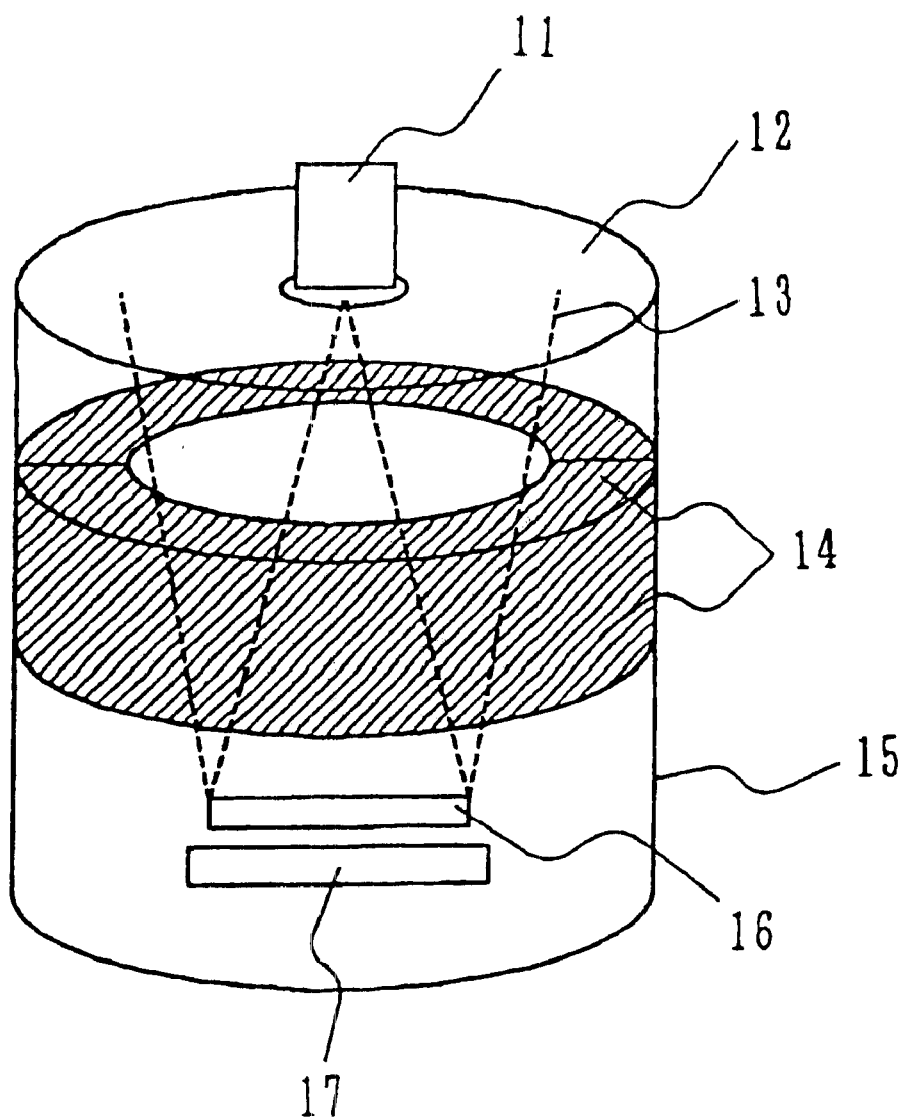

DEVICE FOR CHECKING SHEET PACKAGING

FIELD OF THE INVENTION

The present invention generally relates to a sheet wrapping package inspecting device which detects a mingled foreign substance, damage, and/or dirt of a tablet, which may occur during a sheet wrapping process for wrapping the tablet by checking an appearance thereof without contact thereto. More particularly, it relates to a sheet wrapping package inspecting device which observes both the reflected ray and transmitted ray through a TV camera.

BACKGROUND OF THE INVENTION

In this specification, the term "tablet inspection," unless otherwise specified, generally covers the inspection of a sheet wrapping package which includes a tablet and its wrapping/packaging (hereinafter simply referred to as "wrapping") sheet, and detecting a foreign substance in a space of so-called pocket of the wrapping sheet where the tablet is placed. Also, the term "sheet wrapping package inspecting" is widely used to cover the inspection of a part of the object to be wrapped and its wrapping sheet, and a defect inspection for detecting a foreign substance contained in a space of so-called pocket of the wrapping sheet where the part of the object to be wrapped is placed. In addition, the whole object to be inspected, including the part of the object such as the tablet and its wrapping sheet, is simply referred to as a "wrapping sheet," which is distinguished from a "sheet portion (i.e., a sheet)," unless otherwise specified.

A conventional tablet inspection, which is one of the important sheet wrapping package inspections, will be explained herein below.

A portion to be subjected to the tablet inspection is roughly classified into a tablet, a sheet portion for wrapping the tablet, and a so-called pocket for carrying and holding the tablet therein. As for the tablet, checked by the inspection are a character and/or a symbol formed on the tablet, and a crack, split, fold, breakage, dirt, stain, and adhesive of the tablet. As for the sheet portion and the pocket, checked by the inspection are a stain and dirt thereof, a foreign substance, a broken piece of the tablet, a hair, and a fiber mingled during the wrapping process. It is also checked by the inspection whether or not a different tablet is mistakenly contained in the wrapping.

On the other hand, prior to the present invention, two methods, a method called a reflection type and a method called a transmission type, have been considered separately as an individual method of the inspection. In the reflection type inspection method, a ray is emitted to a wrapping sheet from the upper side thereof, and the reflected ray is observed by a TV camera disposed above the wrapping sheet to detect a defect. In the transmission type method, a ray is emitted to the wrapping sheet from the lower side thereof, or the rear side thereof, and the transmitted ray is observed by a TV camera to detect a defect. According to the reflection type method, it is possible to check the shape of the tablet and detect a foreign substance on the tablet and/or a foreign substance mingled in the wrapping sheet. On the other hand, the transmission type method is utilized to detect a foreign substance mingled in the wrapping sheet and check the shape of the tablet.

As mentioned above, two types of conventional tablet inspection methods, i.e., the reflection type method and the transmission type method, have been considered. However, these conventional methods have the following serious drawbacks.

In the reflection method, many highlights are often captured at the pocket because of the multiple reflection effect, the specular reflection effect and the concave-reflector effect, and thus those highlights are detected as false defects. To escape from those phenomena, the pocket were excluded from the object to be inspected by taking a logical mask covering the region of the image corresponding the pocket on the image by detecting the pocket primarily. This causes serious problems in that not only the detection of the pocket is troublesome but also the inspection of the pocket cannot be performed due to the logical mask.

Also, the surface of the sheet somewhat includes the element of the specular reflection, and the element sometimes appears as a highlight on the image. Although highlights appearing on the pocket and the sheet surface produce serious errors as false defects, there have not been any ways to distinguish and exclude such false defects.

In the transmission method, the contrast of a thin foreign substance such as a hair becomes quite low on the transmitted ray image because of diffraction and some other reasons. This causes a serious omission in detecting defects. Further, it is not possible to distinguish whether a defect mingled in the sheet is a broken piece of the tablet or a foreign substance such as dust, although it is one of the most important issues of the inspection.

As mentioned above, it has not been possible to distinguish and detect serious defects including all defects constantly by either method.

Furthermore, even the combination of these methods could not detect every defects precisely across whole regions at all.

The objective of the present invention is to provide the sheet wrapping package inspecting device that solves the above-mentioned problems and can easily and precisely detect all defects including defects in the pocket.

DISCLOSURE OF THE INVENTION

The sheet wrapping package inspecting device according to the present invention includes a light source and a two-dimensional sensor located above a wrapping sheet respectively, means for inputting a reflected ray image above the wrapping sheet and a light source located below the sheet wrapping and means for inputting a transmitted ray image. The device plots a plurality of several binary or multi-value images of the gained reflected ray image and transmitted ray image, creates density code distribution maps of those images, and thereafter detects defects such as a mingled foreign substance, a damage and/or dirt of a part of a whole object to be inspected, the wrapping sheet and the pocket according to the code distribution maps.

In addition, also disclosed herein is a defect discrimination method in which a logical operation between images have been performed to discriminate a defect based on the logical operation results.

In addition, the device detects a defect by dividing the inputted image into several regions according to the brightness distribution or the code distribution of the inputted image and thereafter giving a code of the neighboring region as an auxiliary code to the code value of each divided region.

To prevent the omission of detecting a defect, the device is provided with a half-mirror or a reflection mirror that reflects at least five percent (%) of the incident light; the reflector is located right under the wrapping sheet.

On the other hand, to enhance the inspection efficiency, the device includes:

light means including light sources located above and below a wrapping sheet, the light sources having different color spectra, or light means including light sources located above and below the wrapping sheet and color filters located between the wrapping sheet and each light source, respectively, the color filters having different color spectra; and two-dimensional sensor located above the wrapping sheet, wherein a two dimension image is inputted while the light sources on both sides of the wrapping sheet are illuminated simultaneously, and the reflected ray image and the transmitted ray image are separated according to the color spectrum of each image because the color spectrum corresponds to that of each light source.

Furthermore, the device separates the reflected ray image and the transmitted ray image by removing the common wavelength element of both the light sources by placing color filters that transmit the same wavelength as the transmittance wavelength spectrum.

Also, as a method of detecting a defect without separating the reflected ray image and the transmitted ray image, the way of detecting defects by adjusting the ratio of the reflected ray and the transmitted ray with a dimmer, and inputting and multi-valuing images of such rays are applicable.

BRIEF DESCRIPTION OF THE DRAWINGS

FIG. 11 is a chart of the detection probability when connecting the dimmers to the power supply according to a third embodiment of the present invention;

FIG. 14 illustrates a flow chart showing the determining procedure of the color of the reflector according to the present invention; and FIG. 15 illustrates a perspective view showing the allocation of the light source according to an embodiment.

BEST EMBODIMENTS FOR EXECUTING THE INVENTION

Embodiments of the present invention will be explained in detail as follows.

Figure 2:
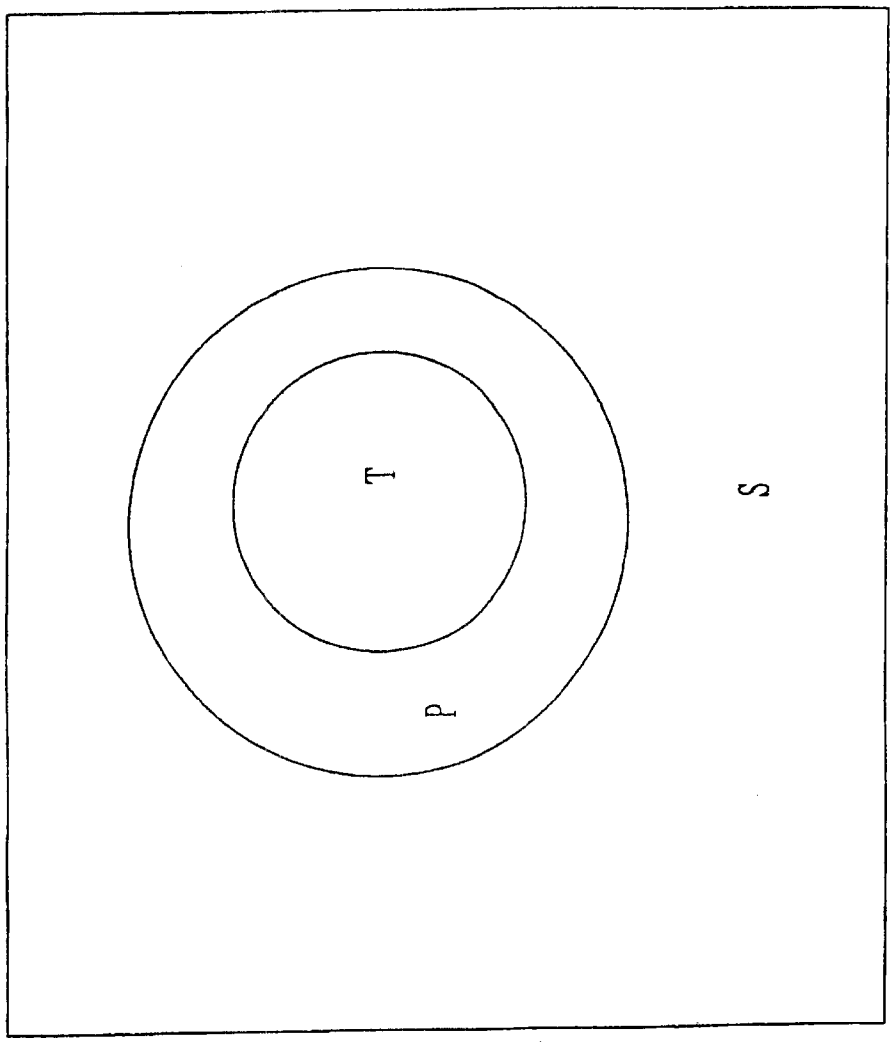
FIG. 2 is a plane view showing the structure of the wrapped tablet according to an object of the inspection of the present invention.

FIGS. 2 and 3 illustrate a plane view and a side cross-sectional view of a wrapped tablet which is an object to be inspected by the present invention, respectively.

Figure 3A:
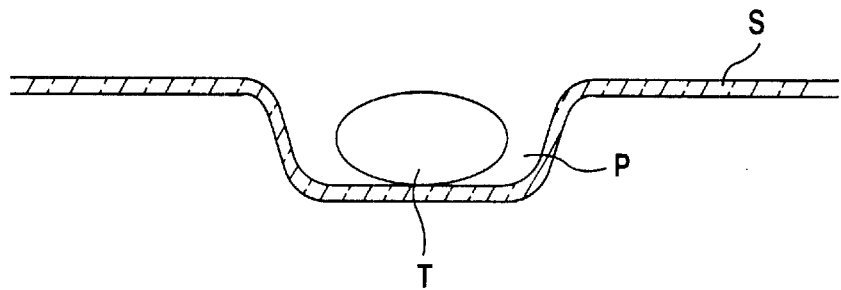
FIG. 3 is a cross-sectional view of the pocket according to an object of the inspection of the present invention.
Figure 3B:
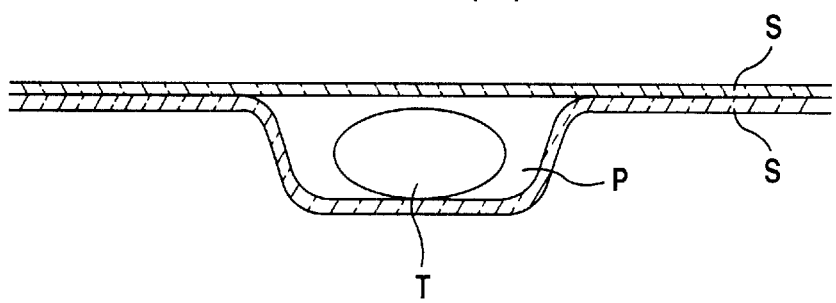

Generally, a plurality of wrapped tablets are placed in a row at an interval of from several millimeters to ten and several millimeters. For simplicity, FIG. 2 shows only one tablet T among wrapped tablets. FIG. 2 is a plane view of a tablet T in a pocket P. Meanwhile, FIG. 3 illustrates the cross-sectional views of the pocket P in which the tablet T is placed. In the wrapping process, one tablet T is placed on a concave spot of the sheet S, which is called the pocket P as shown in FIG. 3(a). Then, another sheet S is attached on the aforementioned sheet S as shown in FIG. 3(b). Although the attached another sheet S is called as a seal and should be distinguished from the sheet S shown in FIG. 3(a), both sheets are called "sheet," respectively and not specifically distinguished in this embodiment. The inspection regions shown in FIGS. 3(a) and 3(b) are both called wrapping sheets.

Figure 3C:
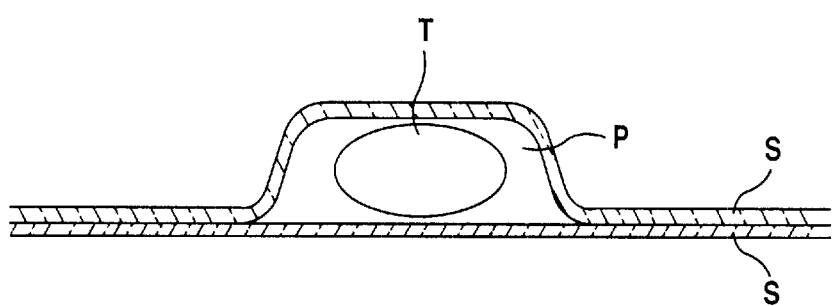

The inspection of the sheet wrapping package can be executed at either condition shown in FIGS. 3(a) to 3(c).

A camera may be placed above or below the wrapping sheet. In this embodiment, the camera is located above the wrapping sheets, and the wrapping sheets shown in FIG. 3(b) is laid up side down as shown in FIG. 3(c). In the inspection method, the location of the camera and the direction of the wrapping sheets may be changed.

Figure 4:
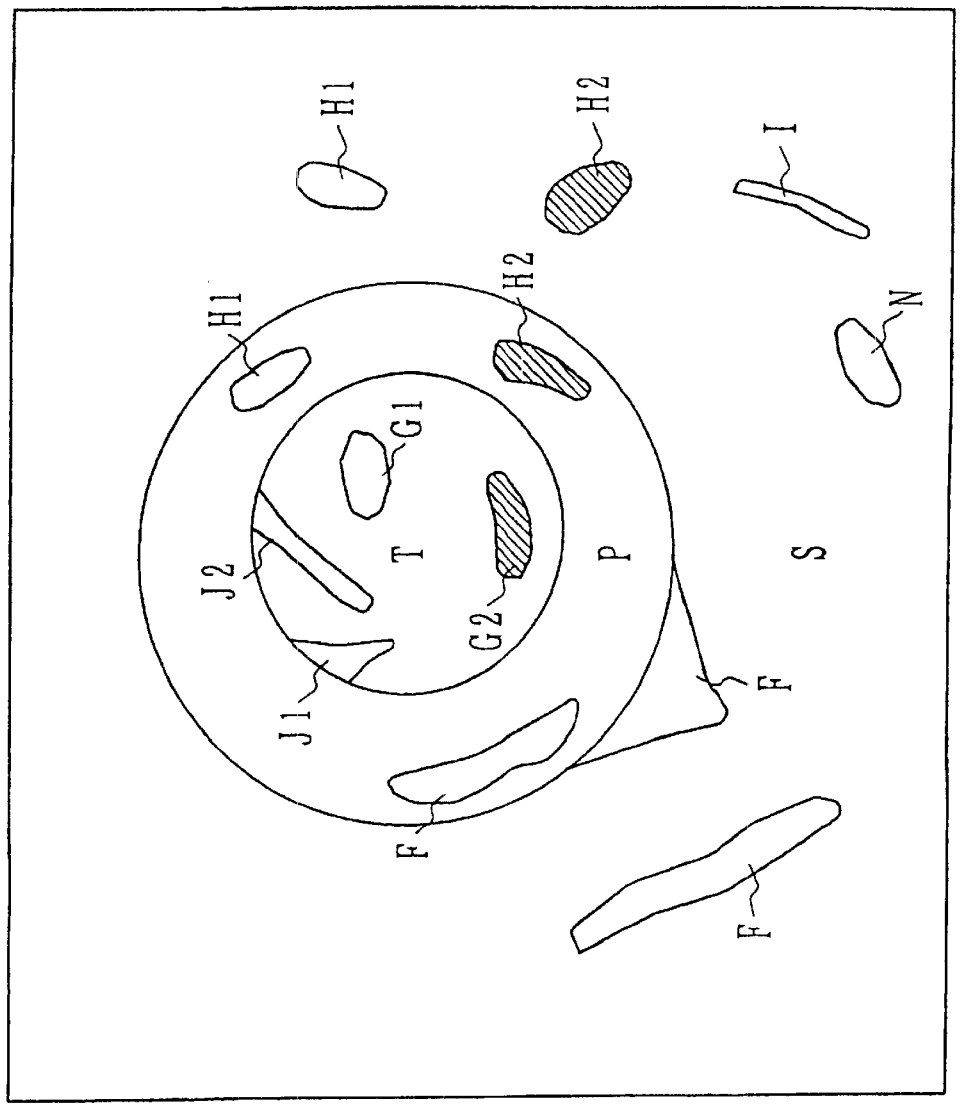
FIG. 4 illustrates the species of the defects according to an object of the inspection of the present invention.

FIG. 4 is an explanatory view showing the species of the defects that contain false defects in the pocket. In this embodiment, the tablet T is white. In FIG. 4, the reference letter F shows highlights caused by the multiple reflection and the concave reflector effect of the pocket, and highlights caused by the specular reflection of the sheet surface. These highlights appear very frequently around the pockets when applying normal illuminations. The reference letter J1 denotes a broken portion of the tablet, and the reference letter J2 denotes a split thereof. The reference letter G1 denotes a while colored defect such as a broken piece of the tablet adhered on it. However, those above-mentioned defects are often undetectable. However, when black edges are observed as outlines of the broken piece adhered to the tablet, the edges are detected as a black foreign substance. The reference letter G2 denotes a mingled foreign substance such as a dust or dirt of the tablet. Cracks of the tablet, the outline pattern of the above-mentioned broken pieces of the tablet, can also be recognized as G2. The reference letter Hi denotes a white foreign substance such as a broken piece of the tablet which is one of the most important defects to be inspected. The reference letter H2 denotes a black foreign substance which is also an important defect to be inspected such as a dirt produced and/or a dust mingled during the wrapping process. The reference letter I denotes a long and an extremely thin and narrow foreign substance such as a piece of hair or fiber, which is one of the most important defects to be inspected. This foreign substance tends to be overlooked by a conventional inspection method utilizing a reflected ray image because of its low contrast. The foreign substance also tends to be overlooked by a conventional inspection method utilizing a transmitted ray because of a diffraction phenomena.

The reference letter N denotes a dirt of the sheet. Although a heavy dirt can be detected as a foreign substance, a dirt whose color is close to that of the sheet often does not appear on the transmitted ray image similar to the defect I. The reference letter N represents this kind of defect distinguished from a defect which is easily be detected.

Figure 5:
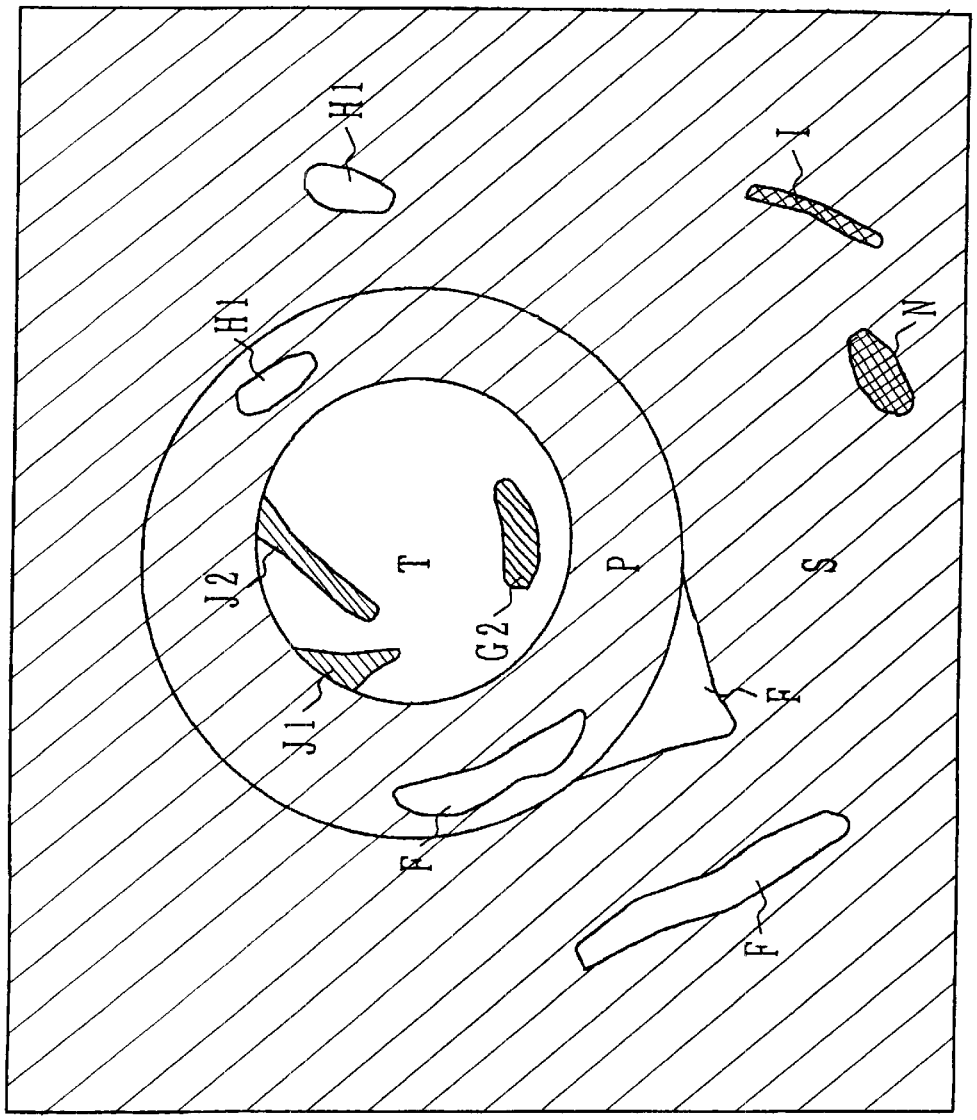
FIG. 5 illustrates a schematic view of the tablet observed from above the tablet, and the brightness of each defect observed from an inputted image.
Figure 6:
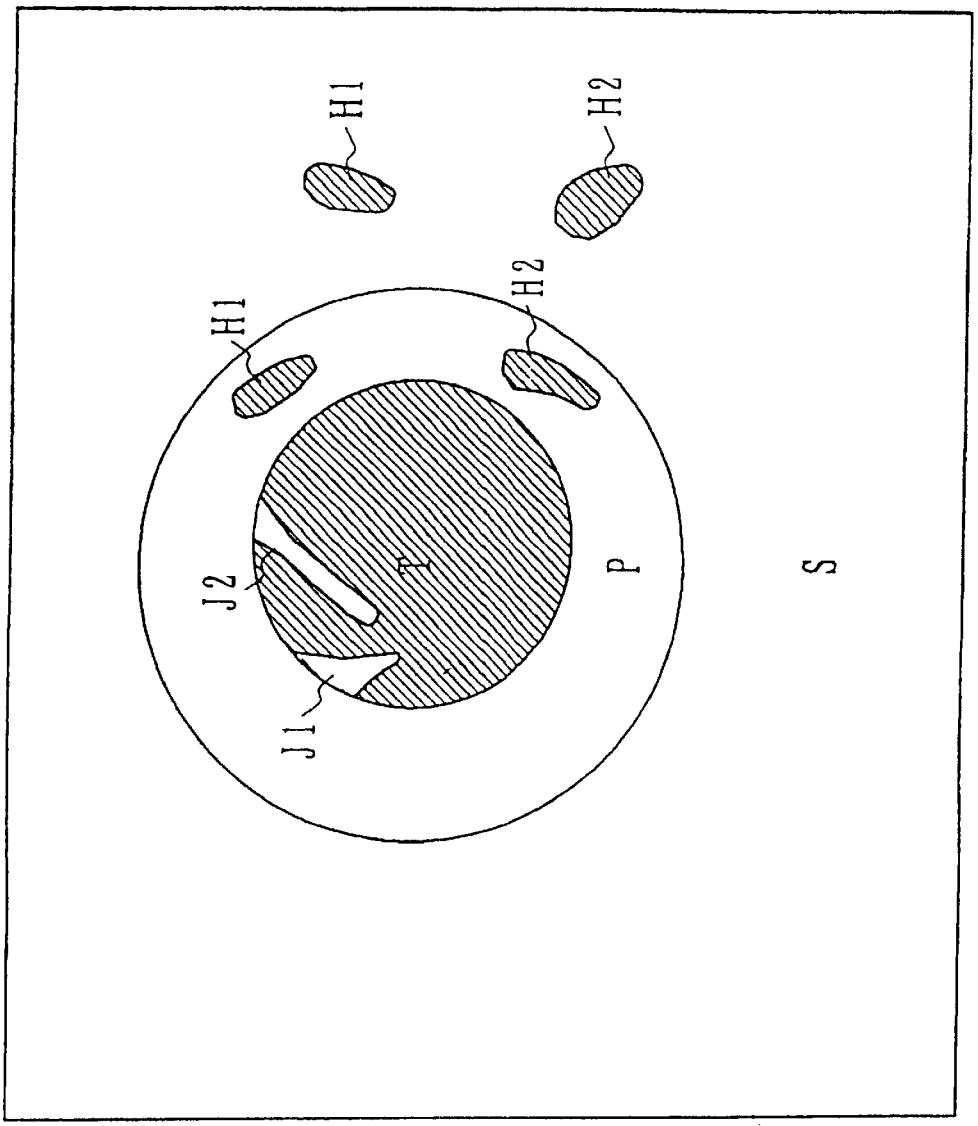
FIG. 6 illustrates a transmitted ray image of the wrapping sheet illuminated by a light source located below the wrapping sheet and captured by a camera placed above the wrapping sheet according to the present inspection.

FIGS. 5 and 6 illustrate how the brightness of each defect is observed from an inputted image.

FIG. 5 illustrates a schematic view of the tablet image observed from above the tablet. In this image, a bright part is shown as a white spot, while a dark part is shown as a black spot. The tablet T, highlights F, and white defects H1 are observed as white spots, but G2 is recognized asa black spots on the white background. As stated above, I and N tends to be overlooked in the reflected ray image because of the low contrasts, and they are hardly detected in the transmitted ray image because of the diffraction phenomena or the extremely small difference of transmittances.

Figure 7:
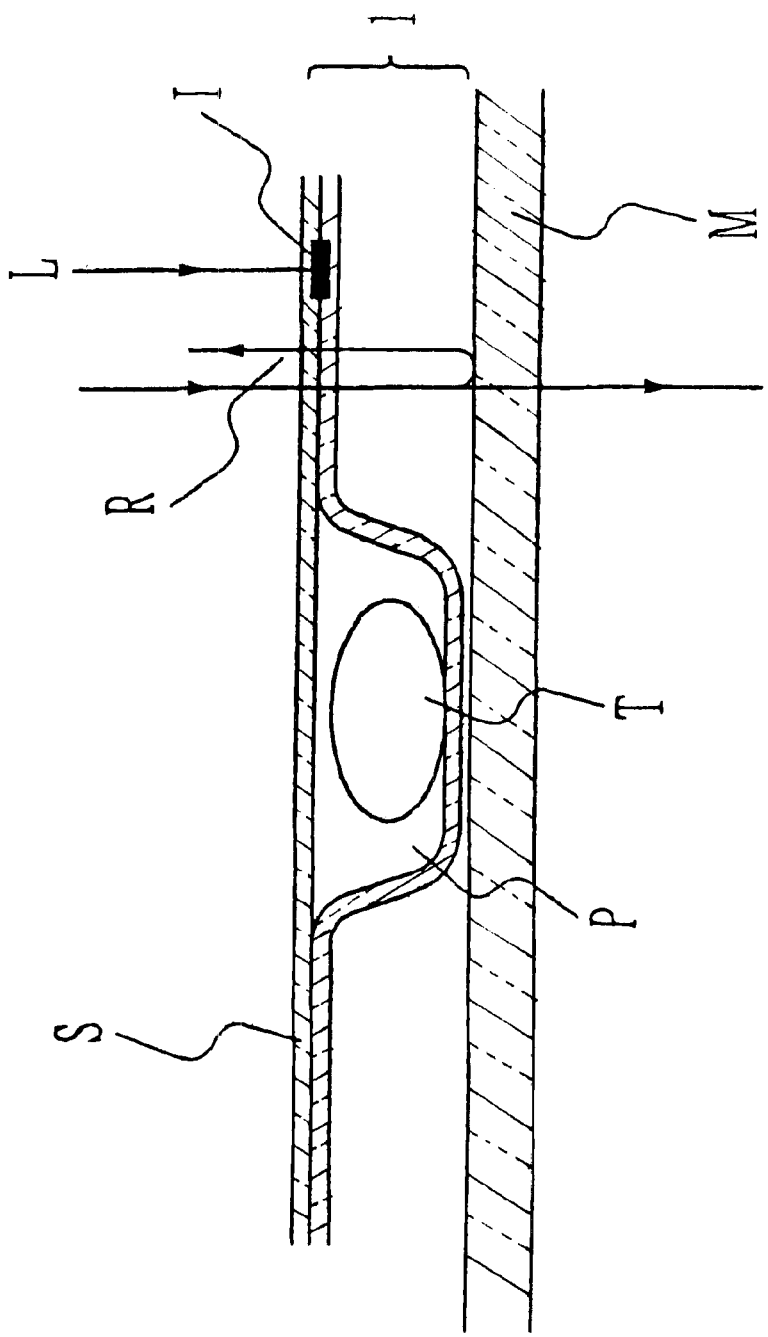
FIG. 7 is an explanatory view showing a method for detecting an extremely thin defect and/or stain-like dirt.

Countermeasures against the above-mentioned problems are explained as follows with reference to FIG. 7. In this invention, a half-mirror M is located under the wrapping sheet 1. Some part of the light which goes through the sheet portion is reflected by the half-mirror M and goes back as a reflected ray R. Where the thin defect I are present, since the reflected ray R does not go back, the portion of the image becomes darker than the other portion of the sheet. Thus, the contrast of the defect is strengthened. This enables a detection of the defect.

Because of the high contrast, N and I are shown darker in FIG. 5. The experiment reveals that the reflectance of the half-mirror should be more than five per cent. A frosted glass that reflects light on its surface can also be applied as a half-mirror.

FIG. 6 illustrates a transmitted ray image of the wrapping sheet illuminated by a light source located below the wrapping sheet and captured by a camera placed above the wrapping sheet. The tablet T, the defects H1 and H2 are observed in black. While the highlight F, the thin defects such as hairs and fibers represented by I often do not appear on the transmitted ray image.

Figures 1A, 1B:
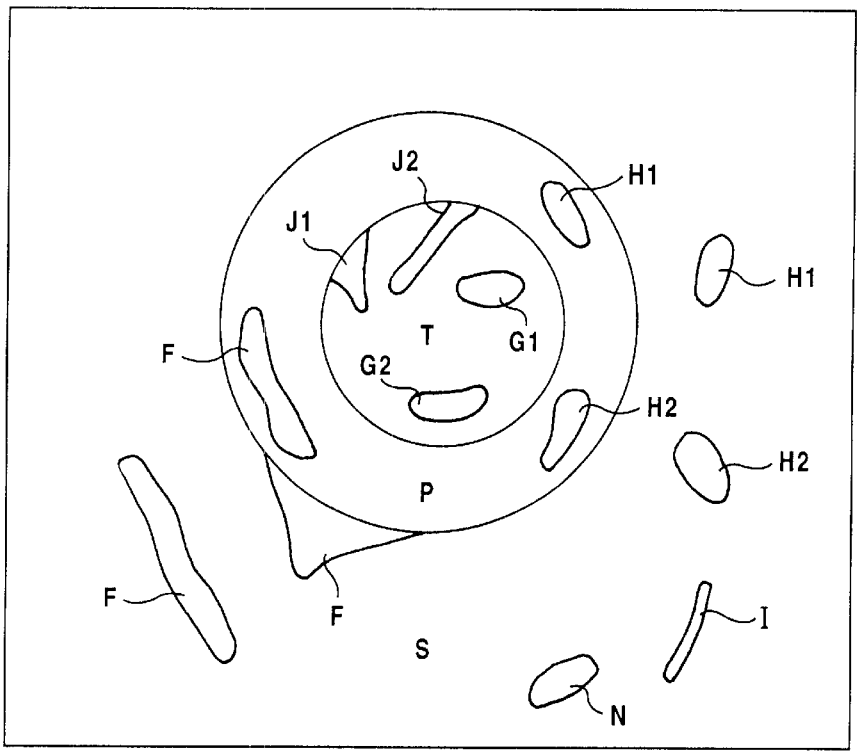
FIG. 1 shows the principle of detecting defects with two kinds of images according to an embodiment of the present invention.

FIG. 1 is a diagram that explains how to detect defects from two image data shown in FIGS. 5 and 6.

FIG. 1(*a*) illustrates a diagram showing defects, and FIG. 1(*b*) is the chart of the code of each defect when expressing FIG. 1(*a*) by codes. Three kinds of coding methods are described: two bit coding, neighboring coding, and four bit coding. Two bit coding expresses each corresponding pixel in FIGS. 5 and 6 by a two bit code: a white pixel as (1) and a black pixel as (0). For example, the tablet T is coded as (10) since it is expressed (1) in the reflected ray image and (0) in the transmitted ray image. Similarly, the defect H2 is coded (00) because it is expressed (0) in both the images. Similarly, F is coded as (11), J1 and J2 as (01), G1 as (10), G2 as (00), H1 as (10), and I as (01). Although the code 01 of I and N are the same as the code 01 of the sheet portion S, codes of I and N are especially coded as (0'1) since I and N can be distinguished from the sheet portion.

Consulting with the two-bit code distribution map FIG. 1(*b*), the existence of defects is recognized. However, J1 and J2 cannot always be defined as defects unless the image processing is performed to recognize the outline of the tablet according to the elementary information about the outline of the tablet. The current embodiment defines those defects by finding the chain of the edge direction.

Neighboring coding is a code distribution map of the code of the neighboring region of each region. The area of each region is relatively small after the image undergoes the labeling processing. However, since J1 can be both (10) and (01), it is fixed to be (11).

Four-bit coding is a distribution map of a code, which includes a neighboring code other than the code of each pixel. After dividing the code map into smaller regions, the specifications of each region such as the center of gravity, area, the shape and the specie are calculated and registered to the list of the defects. Also, positions and species of each defect are displayed with the specific color by allocating a color to each code.

The present invention enables to easy and accurate detection of the position and classification of every defects by creating the code that represents the correlation of the density distribution of the reflected ray image and the transmitted ray image.

Instead of creating code images, it is also possible to detect defects according to the result of the logical calculations of the binary or multi-value images of the reflected ray and the transmitted ray.

The followings are abstracts of the calculation method.

When subjecting AND processing to the binary image of the reflected ray corresponding to FIG. 5 and the binary image of the transmitted ray corresponding to FIG. 6, the only region F, which is bright, is extracted on both images. Meanwhile, when AND processing is executed to the inversion of the reflected ray image, defects J1, J2, I, N and regions P and S that are usually dark in the reflected ray image but bright in the transmitted ray image, are extracted as bright regions. As a result, J1 and J2 can be distinguished because the region T becomes dark in this processed image. N and I can be distinguished by the contrast with S as stated above. When AND processing executed to the inversion of the transmitted ray image instead of the reflected ray image, defects G1 and H1, and the region T, which are usually bright in the reflected ray image but dark in the transmitted ray image, are extracted as bright areas. Since G1 is within the region T, a multi-valuing processing is needed to recognize G1, but defect H1 can be recognized because regions P and S are dark in that image. When AND processing is executed to the inversions of both the reflected ray image and transmitted ray image, only defects G2 and H2 are extracted as bright regions and can be recognized. Instead of AND processing, the combination of XOR, AND, and OR processing are also valid to recognize defects. For example, J1, J2, G1 and H1 can be recognized with the combination of AND and XOR processing, and G2 and H2 can be recognized with AND and NOT processing. However, since cases of applying those combinations are basically the same as that of the combination of the inversions and AND processing, detailed explanations are omitted.

Figure 8:
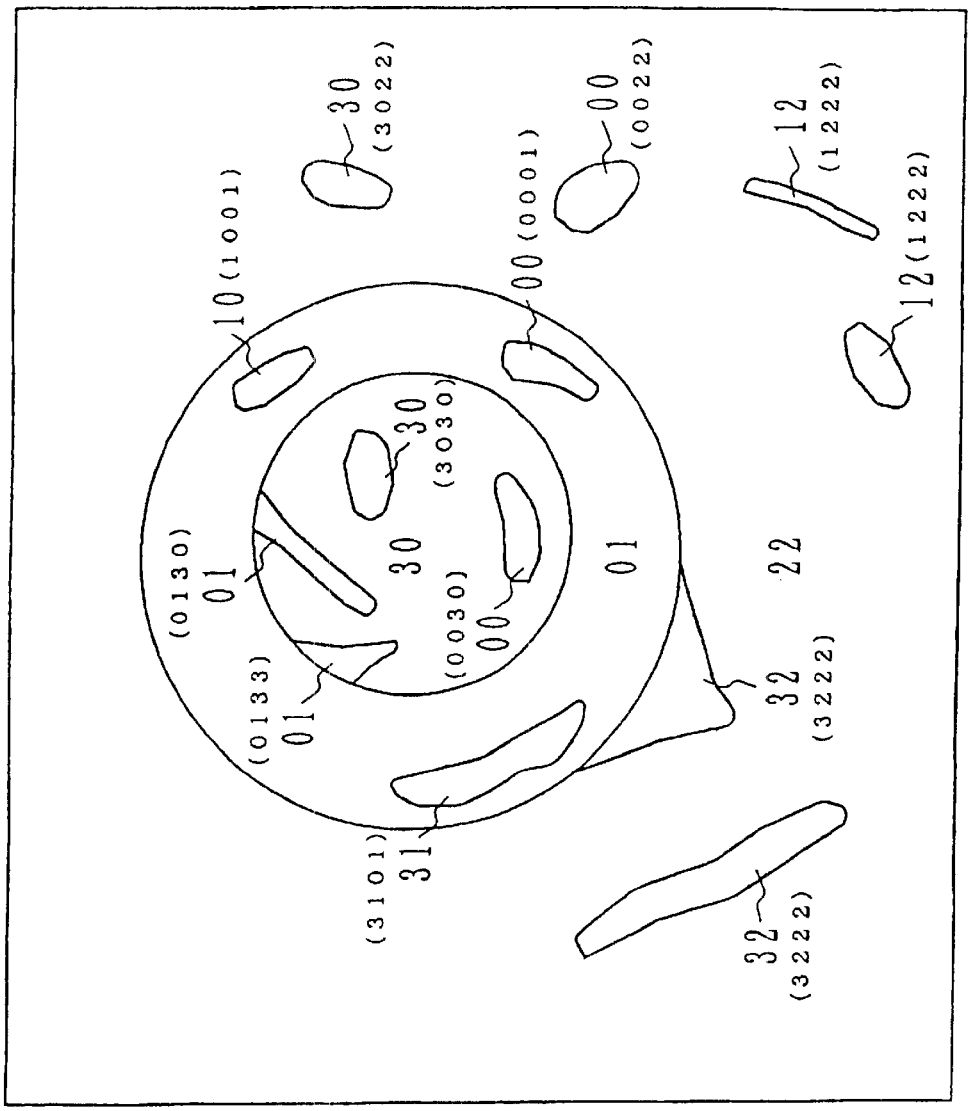
FIG. 8 is a code distribution map prepared by the coding method according to the present invention, wherein the reflected ray image and the transmitted ray image have been quantized into three and four gradations.

FIG. 8 illustrates the code distribution map when quantaizing the reflected ray image and the transmitted ray image into four and three gradations instead of the binarization of the first embodiment shown in FIG. 1.

When the reflectance of the sheet is relatively high, the quantities of the light reflected by the pocket, the defects N and I are smaller than that of the sheet portion. Thus, the reflected ray image is converted into a four-gradation image according to the brightness of the tablet, the pocket, the sheet and the defect I. On the other hand, the transmitted ray image needs to be converted into a three gradation image according to the transmittance of the tablet, the pocket, and the sheet portion for the same reason. The code given to each region is the multi-bit of the reflected ray image and the transmitted ray image that are created by the same procedure as the embodiment shown in FIG. 1, while the code in each parenthesis is the multi-bit with a neighboring code. Thus, it is also possible to recognize defects even more minutely but with only multi-coding of the reflected ray image and the transmitted ray image.

Figure 9:
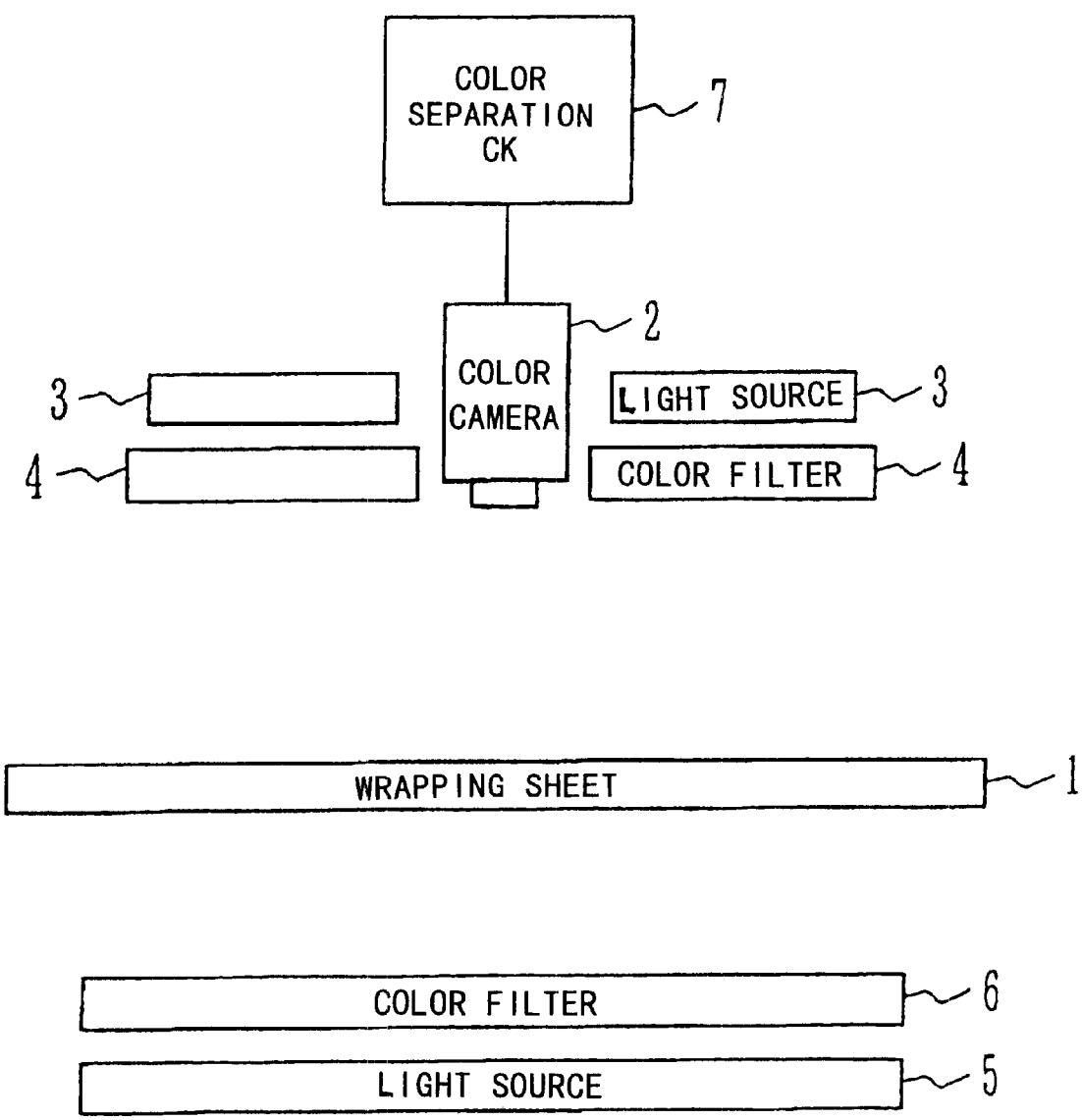
FIG. 9 illustrates a diagram of the structure of the sheet wrapping package inspecting device according to the second embodiment of the present invention.

FIG. 9 illustrates the diagram of the sheet wrapping package inspecting device according to another embodiment of the present invention that captures the reflected ray image and the transmitted ray image simultaneously as one combined image by taking a color filter.

As shown in FIG. 9, the device is equipped with a light source 3 with a band-pass color filter 4 that only transmits the light at the frequency of green, a color camera 2, and a light source 5 with a band-pass color filter 6 that only transmits the light at the frequency of red. While the color camera 2, the light source 3, and the color filter 4 are located above the wrapping sheet 1, the light source 5 and the color filter 6 are located below the wrapping sheet 1. Also, a color separation circuit 7 is connected to the color camera 2 in order to separated the green element and the red element from the input signal.

It is possible to extract the reflected ray image and the transmitted ray image by separating the color signal from the camera with the color separation circuit since the green element signal corresponds to the reflected ray image and the red element signal corresponds to the transmitted ray image; one original image actually contain elements of two images. The method of detecting defects of the current embodiment is the same as the method applied by the first embodiment shown in FIG. 1.

The utilization of above-mentioned embodiment halves the time required for the inspection and simplifies the device because the color filter enables to input the reflected ray image and the transmitted ray image simultaneously on the same image.

There is a risk of lowering actual transmittance when attempting to clear the overlap of the optical wavelength transmittance regions of the filters 4 and 6; the attempt also increases the total cost. Thus, somewhat allowance of the overlap is needed.

Figure 10A:
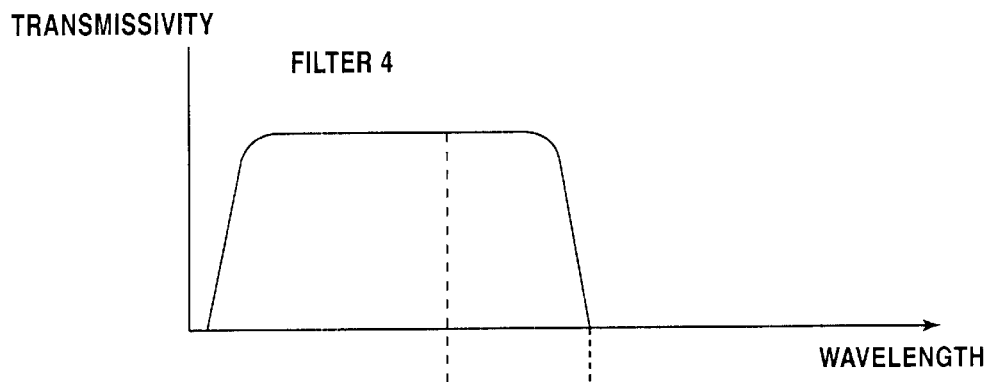
FIG. 10 illustrates a diagram showing the characteristics of the wavelength regions of the optical transmissions when an overlap of the wavelength regions is allowed upon the inspection of the present invention.
Figure 10B:
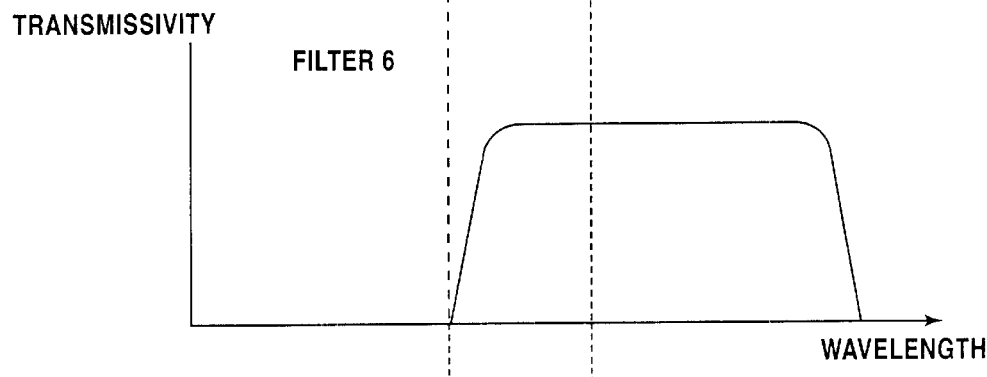
Figure 10C:
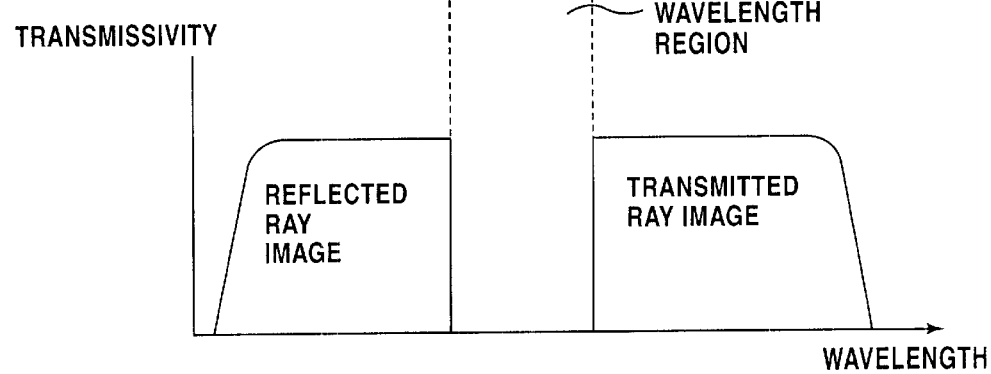

FIG. 10 illustrates the frequency transmittance spectrum of the filters when the optical wavelength transmittance regions overlap each other.

The optical wavelength transmission regions have a common wavelength region of both the filters. Since the wavelength region of the reflected ray image corresponds to the signal of the wavelength region of the illumination for the transmittance from which the common wavelength region is removed, a cheap color filter with high transmittance available on the market can be applicable.

The following is an explanation of a device and a method according to an embodiment of the present invention that detects defects without classifying the reflected ray image and the transmitted ray image. The device inputs images by illuminating lights located at both sides of the wrapping sheet simultaneously and continuously.

A dimmer is connected to each illumination unit located above and below the wrapping sheets to adjust the ratio of the intensities of the reflected ray and the transmitted ray; applicable dimmers are slidacs, ND filters, and color filters. The quantity of the reflected ray and that of the transmitted ray that enter the camera, are compared in consideration of the cases of using colored sheets, and the absorption and the diffusion of the light by the filters.

First of all, the quantity of the transmitted ray is adjusted to be adequately stronger than that of the reflected ray. The input images are processed into four-gradation images because the density distribution is roughly classified into four levels. F is classified into level 1, while J1, J2, I, N, P and S as level 2, G1, H1, and T as level 3, and G2 and H2 as level 4 in order of the brightness. As a result, F can be detected at level 1 because level 1 contains only F. J1 and J2 can be detected at level 2 since level 2 does not contain T, but I and N cannot be detected because level 2 also contains P and S. H1 can be detected at level 3 because of the absence of S and P, but G1 cannot be detected because of T. G2 and H2 can be detected at level 4 because of the absence of S, P, and T. Consequently, this method is weak at detecting the dirt of the same color as the sheet, and the long and thin dusts such as hairs and fibers.

When the quantity of the reflected ray is almost the same as that of the transmitted ray, F, G2 and H2 are the detectable defects according to the above-mentioned procedure. Although N and I are provisionally included within the coverage of the detection, there is the possibility of the omission. In the case when the quantity of the reflected ray is adequately larger than that of the transmitted ray, N and I are detectable as well as F, G2, H1 and H2.

FIG. 11 points the possibility of the detection of each case mentioned above by four levels: ○, Δ, Δ' and x.

The quantity of the reflected ray and that of the transmitted ray are indicated by five levels: large, medium, small the level between large and medium, and the level between medium and small. Although F, G2 and H2 are detectable regardless of the ratio of quantities, the others mostly depend on those quantities, according to the chart. Thus, it is necessary to gain several images at different ratios of quantities of lights. As shown in FIG. 11, when the quantity of the transmitted ray is adjusted to be somewhat large, J1, J2 and H1 can be detected. N and I are expected to be detected by further adjustment of the light. It is clear that the defects are constantly detectable by gaining several images at the different ratios of the quantities of the transmitted ray and the reflected ray, but it is not required to separate the reflected ray image and the transmitted ray image. The above-mentioned method corresponds to the adjustment of the weight coefficient by the dimmer when inputting the combined image of the weighed reflected ray image and the weighed transmitted ray image of the first embodiment.

A half-mirror or a reflecting mirror that matches the required ratio of the transmittance and the reflectance is also applicable instead of the light source below, and it may be used together. Application of a reflecting mirror enhances the contrast of the reflected ray upon the detection of N and I.

Although some explanations of the above-mentioned embodiments applied grated images with FIGS. 1 to 8, those gained images should not necessarily be monochrome because it was to simplify the explanation. It is possible to detect defects and separate the components according to the density difference of the colors, or the grated images of the particular color or the color distribution of the particular color itself because components of the sheet wrapping, the dirt and the foreign substances such as other species of tablets or dusts have their own color specifications. The followings are the embodiment which positively utilizes characteristics of colors.

FIG. 12 illustrates an embodiment which utilizes characteristics of colors.

The structure of the sheet wrapping is the same as the structure shown in FIG. 4.

Figures 12A, 12B:
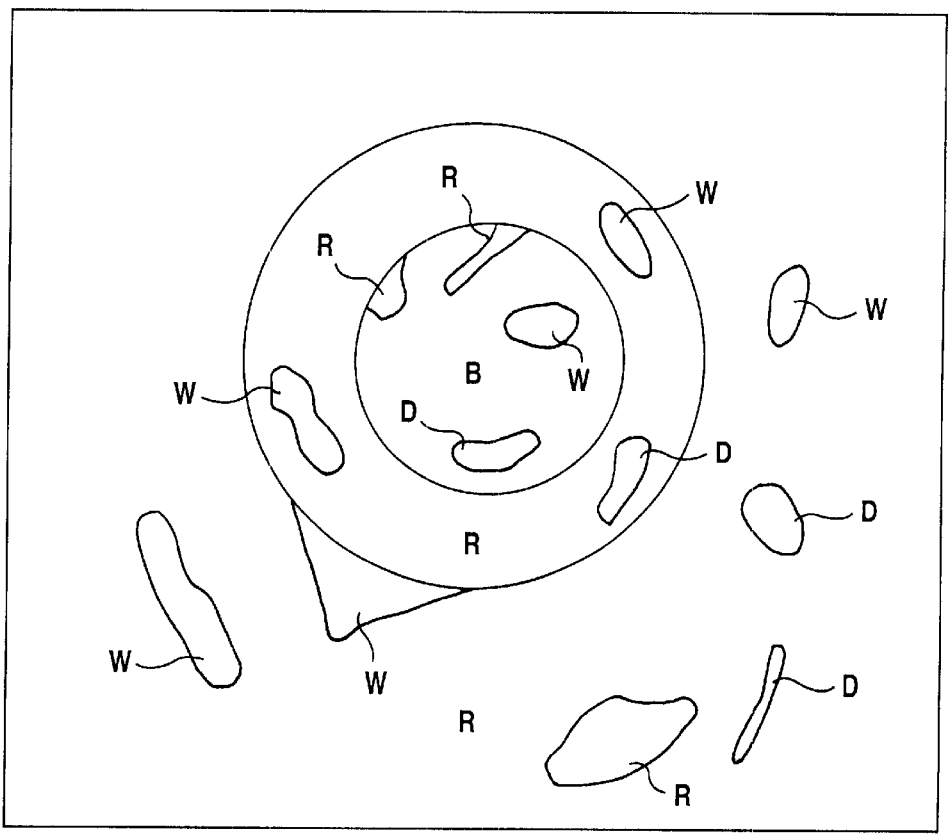
FIG. 12 illustrates the diagram and the chart of an embodiment according to the present invention in which colors have been used.

As shown in FIG. 12(a), the color of the sheet S and the pocket P are defined as red R, the tablet T as blue B, the white foreign substances G1 and H1 as white W, and the black foreign substances G2 and H2 as black D. FIG. 12(b) shows the chart of the color of every part on both the reflected ray image and transmitted ray image. Colors are expressed by the RGB color system. In the reflected ray image, the split J2 and the broken portion J1 are expressed as (100), the highlight F as (111), the tablet T as (001), the foreign substances G1 and H1 as (111), the foreign substances G2 and H2 as (000), the thin hairs and fibers as (000), the dirt as (100), and the sheet S and the pocket P as (100). Although the color of thin hairs and fibers is provisionally defined as (000), it largely depends on the cause. In the transmitted ray image, the sheet, the pocket, the highlight and the dirt on the sheet are expressed as (100), and the others as (000). It is possible to express the colors by the six-bit codes, which are the combination of codes of the reflected ray image and the transmitted ray image.

It is also possible to classify the colors of each part respectively by the logical calculations such as AND and OR processing.

On the other hand, when only regions of red (R) of both the distribution maps of the reflected ray image and the transmitted ray image are picked, and undergo AND processing and inversion, only regions that are red such as the sheet S, the pocket P, the split J2, the broken portion J1, and the dirt N are extracted. When red (R) and blue (B) regions of the images are picked and the regions undergo AND processing and inversion, only foreign substances G1, G1, H1, H2 and I are extracted from the gained grated images. Also, when regions that contain elements of red R or blue B are picked and undergo OR processing and inversion, only black defects G2, H2 and I are extracted.

As stated above, it is possible to recognize each part by creating color code distribution map according to the color distribution or picking the regions that contain one or more colors, or by the logical calculations of the color distributions.

However, if more than two regions whose colors are the same are in one image, it becomes extremely difficult to separate the color regions. More minute classification of the colors prevents the problem. As the methods of more minute classification, comparison and classification of the hues and the saturation, and the comparison of the difference of intensities are applicable. The combination of the classification of densities shown in FIG. 1 and the classification of colors shown in FIG. 12 are also practical. When applying the combination of both ways of above-mentioned classifications of the color and the density, the precision of the recognition remarkably progresses. In this specification, the terms "color analysis" and "color classification" include such combinations.

When regarding the color of the source of the light shown in FIG. 12(a) as blue B, intensities of the tablet T and white color of white foreign substances G1 and H1 are emphasized while intensities of the other regions are weakened in the captured image because the color distribution of the image depends on that of the light source. When the light source is green, color intensities of the parts other than white foreign substances are weakened. To choose the color of the light source best corresponding to the colors of the components, foreign substances and the dirt of the sheet is crucial to recognize each part by the intensities of the colors or the density distribution. In addition, other species of tablets whose colors are different from the object to be inspected can be recognized when comparing the relationship between the color of the light source and the captured image of the object to be inspected and the standard data. Standard data are the information of the relationship between the color of the light source and that of the captured image of the defectless sample sheet wrappings. The standard data must be recorded prior to the inspection.

It is recommended not to fix the color of the source of the light in advance because the optimum color of the light source varies depending on the colors of the components of the sheet wrapping, the foreign substances, and the dirt. Thus, the color of the light source should be flexibly changeable. To gain the optimum color of the light source easily, an illumination unit consisting of several LEDs or miniature bulbs with a dimmer is required. The LEDs or bulbs emit at least one of three elements of the color such as R, G or B. Also, the dimmer should be able to adjust the electric current of each color of the light source independently. As another method, attaching a color filter to the light source is also applicable. By attaching different filters, the color can also be adjusted.

It is possible to recognize the component parts of the sheets and the defects by the color difference in the captured image by just choosing the color reflector. When taking a color reflector such as a color half-mirror or a color reflecting mirror whose reflectance is at least five per cent, which is located under the sheet wrapping instead of the light source, the sheet wrapping is illuminated by the light of the color corresponding to the color of the reflector instead of the light source. Yet in this case, the only light that contains the elements of the color of the light emitted from the light source that overlap with elements of color of each part of the sheet wrapping is transmitted through the sheet wrappings and enter the reflector. Then, the only color elements that match the color elements of the reflector are reflected by the reflector, transmitted through the sheet wrappings, and captured by the two-dimensional sensor as an image.

The above-mentioned embodiment will be explained with reference to FIG. 13.

The color of each part of the sheet wrapping is the color shown in FIG. 12(a), and each part contains the sub color element/s as well as the main color elements.

Figure 13A:
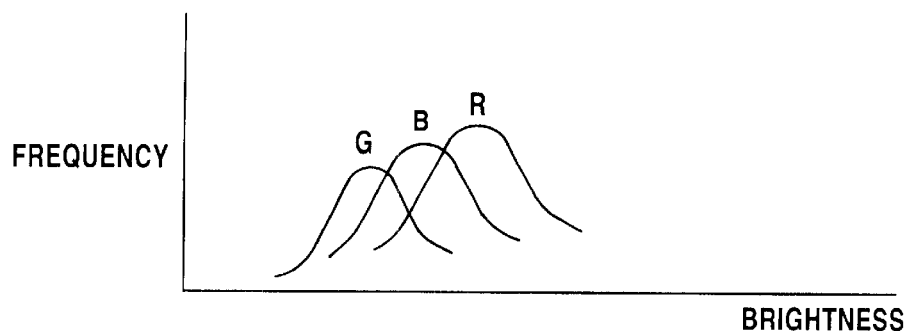
FIG. 13 illustrates an embodiment showing the principle of heightening the color contrast.
Figure 13B:
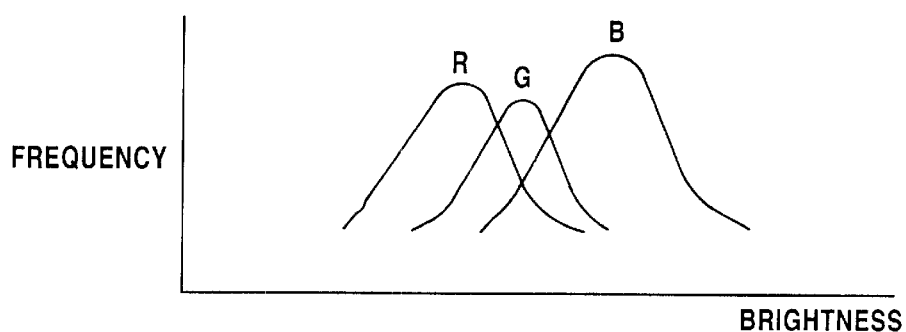
Figure 13C:
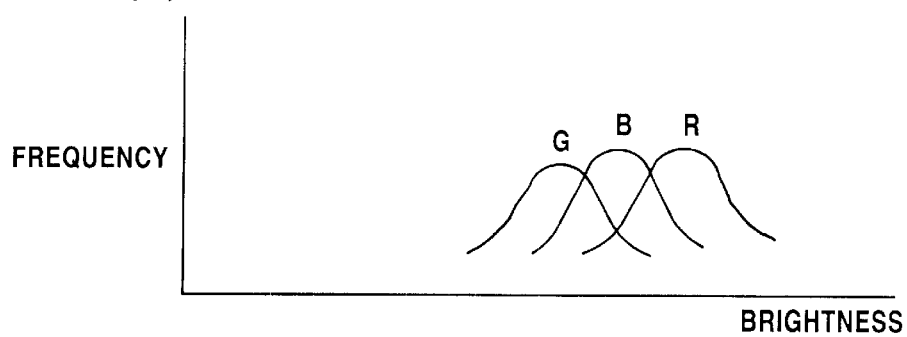

FIGS. 13(a) and 13(b) show the histogram of each color element of the sheet color and the histogram about the tablet. FIG. 13(c) shows the histogram of each color element of the sheet color when a white reflector is placed below the sheet, the whole region becomes brighter by the reflection, but the ratio of the color elements does not change. On the other hand, histogram of the region of the tablet does not change from (b).

Figure 13D:
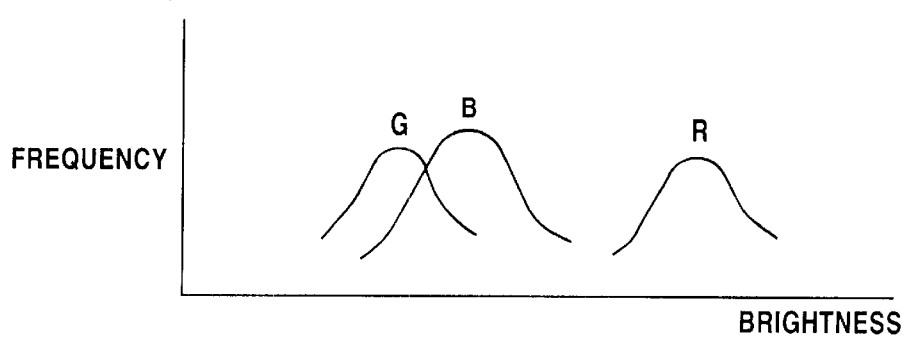

In the case when the reflector is changed to a red one, there are little reflections of blue and green lights though the red light is strongly reflected. Relatively, only the element of red of the sheet is stressed while the intensity of the blue element, which is the same as the color of the tablet is lowered because the red light is fully reflected by the reflector and captured, but the only blue and green lights contained by the original light are reflected by the sheet and captured. As a result, the color contrast of the red color of the sheet and the blue color of the tablet becomes strikingly vivid as the histogram of FIG. 13(d) shows the element of red is outstandingly stronger than the other elements.

It seems to be problematic if the color of the tablet is also red. In such cases, the red of the tablet is relatively stressed by weakening the intensity of the red of the reflector if the color of the tablet is more dense than the sheet. By stressing the complementary color element green of the sheet while weakening the intensity of red of the sheet with a green reflector, a strong contrast between green of the sheet and red of the tablet can be obtained when the quantities of green of the tablet and the sheet are either small or the same.

The method of stressing the color contrast is summarized as follows. To obtain a strong color contrast, it is recommended to heighten the reflectance of the reflector about the color of the sheet, or the color element that sheet contains more than the tablet, and to lower the reflectance of the color element that tablet contains more than the sheet as much as possible, as a result of the comparison between the density of each color element R, G, and B of the sheet and the tablet; to lower the reflectance, deducting the color element from the reflector is applicable. When the tablet and the sheet do not include the complementary color elements, or the quantities of such elements included are very close each other, more stressed color contrast can be obtained by combining other color elements, especially the complementary color elements as the reflector. This method is also applicable when each color element R, G and B of the color of the sheet is brighter than that of the tablet, by applying a white reflector that reflects every color element of the color. On the contrary, when each color element R, G and B of the color of the sheet is darker than that of the tablet, it is recommended to remove the reflector, or to choose a black reflector that does not reflect the light at all. As stated above, using a reflector that highly reflects the color elements which the transmitter such as the sheet more highly contain than the non-transmitter such as the tablet, or choosing a reflector that lowly reflects the color elements which the non-reflector more highly contain than the transmitter eases the classification of the regions according to the color analysis because the color contrast between the transmitter and the non-transmitter becomes stronger. On the current embodiment, the color elements are classified and explained by the RGB color system, but the RGB color system is not necessarily the only system because there are various kinds of color systems.

FIG. 14 is the explanation of determining the color of the reflector corresponding to the current embodiment. In FIG. 14, the letter C stands for the color elements, while the letter S stands for the sheet, the letter T stands for the tablet, and the letter H stands for the complementary color. The combination of color elements is determined according to the procedure shown in FIG. 14, but each color element is processed separately.

When the color of the sheet contains more quantity of the color elements of the color of the tablet (step 101), the color element of the sheet is further stressed (step 106). On the contrary, when the color of the sheet contains less quantity of the color element than the color of the tablet, the complementary color (step 102) is regarded and stressed (step 104), and the intensity of the color of the sheet is then deducted when Hs is close enough to Ht or Hs=Ht (step 103). When not regarding the complementary color or Hs is not equal to Ht, the color element of the sheet is directly deducted (step 105). The procedure needs to be repeated three times when the colors are classified by the RGB color system. Also, setting the judgment N as the preference can pass the step 102 .

Sometimes many strong highlights and ghosts occur and appear in the captured image because of the specular reflection on the surface of the reflector such as a mirror or a color reflector (hereinafter simply referred to as "reflector"). Also, some parts of the camera, the surrounding atmosphere or/and the sheet wrapping is/are captured by the camera and appear/s in the image. It is recommended to process the surface of the reflector into the light-diffusing surface by putting fine unevenness as the countermeasure. Also, to decrease the shadings, the surface of the whole reflector should be concave because when the field of vision is broad, shadings appear very frequently. The reason of forming the surface of the reflector concave is to offset the Lambert's cosine law.

In a case where any parts of the surface of the tablet are specular, it is necessary to secure certain distance between the camera and the optical path from the light source, and the optical path of the specular reflection because the light source and/or the camera itself is captured by the camera and appear in the images.

FIG. 15 illustrates the location of the light source of the current embodiment.

The light source is located cylindrically in the space between the camera 11 and the sheet wrapping 16, and the atmosphere other than the light source is surrounded by the black board 12. A two-dimensional tri-color LED alley 14 is applied as the light source, and a frosted glass or a white diffuser that transmits the light is located in front of the LED alley 14 to prevent the camera 11 from capturing the light source that appears as the ghosts on the image. Although the current embodiment locates the light source cylindrically, the arrangement of the light source should not necessarily be cylindrical. Color miniature bulb can be also used instead of the color LED alley 14.

Shades of the tablets and the foreign substances are observed on the reflector 17 when irradiating the light from the upper side of the sheet wrappings 16 with locating the reflector 17 below the sheet wrapping 16. Those shades are obstacles to detect defects if the camera captures them. It was clarified that when securing the distance between the sheet wrapping 16 and the reflector 17 far enough, the problem can be prevented. According to the experiment, the distance between the sheet wrapping 16 and the reflector 17 should be approximately at least more than 10 mm though it depends on the characteristics of the lens, the location of the camera 11, and the arrangement of the light source.

Since the reflectance and the transmittance of the wrapped portion, the sheet portion and the pocket are different, the brightness distribution captured by the TV camera is tremendously different between the images gained. Also, reflectance and the transmittance of the defects are also different depending on species, sizes, and positions of the foreign substances. Thus, the reflected ray image and the transmitted ray image possess different characteristics of the brightness distribution each other. The focus of the present invention is the full utilization of such characteristics.

The present invention can recognize and detect stuck foreign substances, mingled foreign substances, tablets of other species, transformation of the wrapped object, the broken pieces, the dirt, extremely thin hairs and fibers around all regions of the wrapped object, the sheet and the pocket quite precisely because the defects are detected according to the logical correlation between image data of the reflected ray image and the transmitted ray image. Those images can be input simultaneously without changing the positions of the camera and the wrapping sheets.

As a result of heightening the efficiency of utilizing both methods of reflection and transmission by inputting the reflected ray image and the transmitted ray image simultaneously on the condition of using the illumination of specific colors, it becomes possible to escape from the complication of the device because there is no need to input several images by changing methods. Since the device inputs the reflected ray image and the transmitted ray image simultaneously, the present invention can also escape from the omission of the detection and the detection of the false defects.

Although two band-pass color filters are used in the above-mentioned embodiments, low-pass or high-pass color filters can also be used. The combination of the colors of filters other than green and red is also applicable. What is the most important is to choose the color filter that most precisely corresponds to the colors of the sheet and the tablet so that the most vivid contrast of the shade can be gained. Instead of using such color filters, light sources that can emit the light at several different wavelengths such as LEDs that emit the light at several levels of wavelengths can be used. Although a TV camera is applied in the above-mentioned embodiments, other kind of two-dimensional sensors such as a far-infrared camera, an X-ray camera, or a silver-chloride film is also applicable. It is to possible to capture a two-dimensional image by scanning a line sensor as well. The line sensor is regarded as a two dimensional sensor. In the present invention, monochrome sensors and color sensors are both defined as two dimensional sensors or cameras.

There is no problem to position the camera below the wrapping sheet though it is positioned above on this statement, the angle of the camera is also arbitrary.

Although the aforementioned embodiments are directed to a device for detecting a defect in the tablet wrapping process, the present invention is not limited to it. The present invention can also be applied to other types of inspections such as the inspection of any other objects on or enclosed by the wrapping sheet.

POTENTIALITY OF THE INDUSTRIAL USE

As explained above, the present invention enables precise and easy detection of defects according to the codes that represent the correlation of brightness distributions, or the color distribution of the reflected ray image and the transmitted ray image of the wrapping sheets that are illuminated from above and below simultaneously or one by one. Those images are captured by a TV camera. The present invention also allows classification of defects by adding the code of the neighboring region after the area division. Locating a half-mirror or a reflector right under the wrapping sheet enables detection of the mingled hairs and fibers that are extremely thin. By illuminating the object of the light with two kinds of lights that have different characteristics of color emission for the reflection and the transmission simultaneously, the reflected ray and the transmitted ray image can be within one image. This method slashes the time-related control of the light sources and also halves the number of the input images. Thus, the inspection can be executed within shorter time but constantly. The countermeasures of the situation when the separation of the reflected ray image and the transmitted ray image, are also disclosed as the method of detecting defects by not separating those images. Finally, it is possible to stress the color contrast by heightening the reflectance of the reflector about the particular color that is more highly contained by the sheet, or the same color as the sheet, and lowering the reflectance of the reflector about the color that tablets more highly contain, after comparing the intensities of RGB elements of tablets and the sheet one by one.

What is claimed is:

1. A sheet wrapping package inspecting device which detects a defect of at least one of a wrapping sheet and an object to be wrapped, such as at least one of shape, crack, broken piece, dirt, stain, mixed foreign material and the like, comprising:

a first light source (3; 14) for lightening the wrapping sheet (1; 16), said first light source being located at a first side of the wrapping sheet;

a second light source (5; 14, 17), for lightening the wrapping sheet (1; 16), said second light source being located at a second side of the wrapping sheet;

a two-dimensional sensor (2; 11) located at one of said first and second sides of the wrapping sheet and object (1; 16), for observing the wrapping sheet and object so as to produce signals of a reflected ray image of said wrapping sheet and object by light rays originating from one of said first and second light sources, and signals of a transmitted ray image of said wrapping sheet and object by light rays originating by the other of said first and second light sources; and a signal processing means (7) being provided for putting signals derived from said reflected ray image and from the transmitted ray image into mutual relationship, wherein said signal processing means (7) is provided for binarization or multi-valuing of the reflected ray image and of the transmitted ray image so as to create a code distribution image.

2. A sheet wrapping package inspecting device as recited in claim 1, wherein said second light source (5, 17) is formed by said first light source (14) and by a reflector (17) or a half-mirror (M) which is arranged to receive light from said first light source through the wrapping sheet and object (16) to be inspected, and to reflect received light back through said wrapping sheet and object, and wherein said two-dimensional sensor (11) is arranged on the same side of said the wrapping sheet and object (16) as said first light source (14).

3. A sheet wrapping package inspecting device as recited in claim 2, wherein the half-mirror (M) or the reflecting plate (17) is a color half-mirror or a color reflecting plate having a reflective characteristic depending on color or wavelength of the incidence light, and wherein the reflective characteristic is selected or adjusted such that the color distribution or the density distribution of respective portions of the wrapping sheet and object is enhanced, weakened or changed to improve color contrast of the respective portions.

4. A sheet wrapping package inspecting device as recited in claim 3, wherein the color of the half-mirror (M) or the reflecting plate (17) is selected or adjusted such that, regarding a color component to be enhanced in the transmitted ray image region of a portion of the wrapping sheet and object to be observed, the color component is increased, while regarding color component to be decreased in the image region, the color component is decreased.

5. A sheet wrapping package inspecting device as recited in claim 3, wherein the color of the half-mirror (M) or the reflecting plate (17) is prepared by mixing a first color component to be enhanced in the transmitted ray image region of a portion of the wrapping sheet and object to be observed and a second color component which is a complementary color component of one to be decayed in the image region to be observed.

6. A sheet wrapping package inspecting device as recited in claim 2, wherein each surface of the half-mirror (M) and the reflecting plate (17) is any one of a light diffusion surface, a concave surface and a convex surface.

7. A sheet wrapping package inspecting device as recited in claim 1, wherein the first and second light sources (3, 5) for lightening the wrapping sheet and object (1; 16) are different from each other in at least one of the luminance and chromaticity of respective lights, and wherein a separation circuit (7) is provided for separating the output signals obtained by the two-dimensional sensor (2; 11) into signals of a reflected ray image and a transmitted ray image on the basis of said difference in the light characteristics.

8. A sheet wrapping package inspecting device as recited in claim 1, wherein said code distribution image is provided for showing a plurality of image density distributions or image color distributions.

9. A sheet wrapping package inspecting device as recited in claim 1, wherein the codes of said code distribution image each comprise multi-bit code elements.

10. A sheet wrapping package inspecting device as recited in claim 9, wherein a combination code is created by adding binary or multi-bit code in one region of the code distribution image with binary or multi-bit code in another region adjacent to the one region, and wherein the combination code so created is handled as a multi-bit code of one unit in a logical operation performed thereafter.

11. A sheet wrapping package inspecting device as recited in claim 1, wherein the codes of said code distribution image result from binarizing signals of said reflected ray image and the transmitted ray image and then putting said binarized signals into mutual relationship by logical operation.

12. A sheet wrapping package inspecting device as recited in claim 1, wherein at least one of said first and second light sources is disposed at such a position that the mirror (specular) reflected light component which is irradiated from said at least one light source (specular) reflected at the surface of the wrapping sheet and object and received by the two-dimensional sensor, is reduced or removed.

13. A sheet wrapping package inspecting device as recited in claim 1, wherein the logical operation is composed of at least one of the logical operations XOR, AND, OR and NOT.

14. A sheet wrapping package inspecting method for detecting a defect of a wrapping sheet and an object to be wrapped, such as shape, crack, broken piece, dirt, stain, mixed foreign material, or the like, comprising the steps of:

lightening the wrapping sheet (1; 16) and object from a first side;

lightening the wrapping sheet (1; 16) and object from a second side;

observing the wrapping sheet and object so as to produce signals of a reflected ray image of said wrapping sheet and object and of a transmitted ray image of said wrapping sheet and object by light rays; and being provided signal processing for putting signals derived from said reflected ray image and from the transmitted ray image into mutual relationship, wherein said signal processing is provided for binarization or multi-valuing of the reflected ray image and of the transmitted ray image so as to create a code distribution image.

15. A sheet wrapping package inspecting method as recited in claim 14, wherein lightening of said wrapping sheet and an object is performed from a first side directly and from a second side by interposition of a reflector (17) or half-mirror (M) arranged to receive light from said first side through the wrapping sheet and object (16) to be inspected, and to reflect received light back through said wrapping sheet and object.

16. A sheet wrapping package inspecting method as recited in claim 14, further comprising the steps of:

performing simultaneously illuminations from first and second sides with light rays being different from each other in at least one of luminance and chromaticity of the illuminations to take a reflected ray image and a transmitted ray image simultaneously; and separating the signals of the reflected ray image and the transmitted ray image taken simultaneously on the basis of the difference in the light characteristic.

17. A sheet wrapping package inspecting method as recited in claim 14, further comprising the steps of:

performing simultaneously illuminations from first and second sides with light rays which have wavelength distributions different from each other but include a common wavelength component and which are different in at least one of luminance and chromaticity of the illuminations to take a reflected ray image and a transmitted ray image simultaneously;

removing the common wavelength component from the taken image signals; and separating signals of the simultaneously taken reflected ray image and transmitted ray image into the signals of the reflected ray image and the transmitted ray image on the basis of a difference in light characteristic of the illuminations.

18. A sheet wrapping package inspecting method as recited in claim 14, wherein said code distribution image is provided for showing a plurality of image density distributions or image color distributions.

19. A sheet wrapping package inspecting method as recited in claim 14, wherein the codes of said code distribution image each are produced for comprising multi-bit code elements.

20. A sheet wrapping package inspecting method as recited in claim 14, wherein the codes of said code distribution image are obtained by binarizing or multi-valuing the signals of said reflected ray image and the transmitted ray image, and putting said binarized or multi-valued signals, respectively, into mutual relationship by logical operation.

21. A sheet wrapping package inspecting method as recited in claim 14, further comprising the steps of:

in a state where the wrapping sheet (1, 16) and the object are illuminated simultaneously from first and second sides, taking a plurality of density images of the wrapping sheet and the object while changing light intensity ratio of the two illuminations;

performing binarization or multi-valuing on the plurality of density images obtained to detect defects which can be detected under a condition of respective light intensity ratios; and classifying the defects obtained in all the light intensity ratio conditions.

22. A sheet wrapping package inspecting method as recited in claim 21, wherein the light intensity ratio of the first and second illuminations is adjusted such that the ratio of the amount of reflected ray and the amount of transmitted ray becomes optimal according to the color distribution, the reflectivity and transmissivity of the wrapping sheet and the object.

23. A sheet wrapping package inspecting method as recited in claim 14, wherein the logical operation is composed of at least one of the logical operations XOR, AND, OR and NOT.

* * * * *

UNITED STATES PATENT AND TRADEMARK OFFICE
CERTIFICATE OF CORRECTION

PATENT NO.   : 6,445,452 B1
DATED        : September 3, 2002
INVENTOR(S)  : Kondou et al.

It is certified that error appears in the above-identified patent and that said Letters Patent is hereby corrected as shown below:

Title page,
Item [86], "§ 371(c)(1), (2), (4) Date: Dec. 16, 1998" should be -- § 371(c)(1), (2), (4) Date: Dec. 16, 1999 --

Signed and Sealed this

Eleventh Day of March, 2003

JAMES E. ROGAN
*Director of the United States Patent and Trademark Office*